United States Patent [19]
Titone et al.

[11] Patent Number: 5,569,273
[45] Date of Patent: Oct. 29, 1996

[54] SURGICAL MESH FABRIC

[75] Inventors: Milo A. Titone, Wilmington, Del.; Fred D. Herzog, Westford, Mass.

[73] Assignee: C. R. Bard, Inc., Murray Hill, N.J.

[21] Appl. No.: 502,021

[22] Filed: Jul. 13, 1995

[51] Int. Cl.$^6$ .......................... A61B 17/00; A61B 19/00; A61F 2/02; A61F 2/08
[52] U.S. Cl. .................. 606/151; 428/225; 623/11; 623/14; 623/15
[58] Field of Search .................. 606/151; 623/11, 623/14, 15; 428/225

[56] References Cited

U.S. PATENT DOCUMENTS

| | | |
|---|---|---|
| 3,805,301 | 4/1974 | Liebig . |
| 3,853,462 | 12/1974 | Smith . |
| 3,878,565 | 4/1975 | Sauvage . |
| 3,945,052 | 3/1976 | Liebig . |
| 3,986,828 | 10/1976 | Hoffmann et al. . |
| 4,141,087 | 2/1979 | Shalaby et al. ............... 623/11 |
| 4,193,137 | 3/1980 | Heck . |
| 4,347,847 | 9/1982 | Usher . |
| 4,391,106 | 7/1983 | Schafer et al. . |
| 4,452,245 | 6/1984 | Usher . |
| 4,476,697 | 10/1984 | Schafer et al. . |
| 4,652,264 | 3/1987 | Dumican ....................... 623/11 |
| 4,769,038 | 9/1988 | Bendavid et al. . |
| 4,902,508 | 2/1990 | Badylak et al. ................ 623/11 |
| 4,923,470 | 5/1990 | Dumican ....................... 623/11 |
| 4,955,907 | 9/1990 | Ledergerber .................. 623/11 |
| 5,002,551 | 3/1991 | Linksy et al. . |
| 5,007,916 | 4/1991 | Linsky et al. . |
| 5,178,630 | 6/1993 | Schmitt ........................ 623/11 |
| 5,292,328 | 3/1994 | Hain et al. . |
| 5,304,187 | 4/1994 | Smith ......................... 606/151 |
| 5,366,460 | 11/1984 | Eberlach ...................... 606/151 |
| 5,366,504 | 11/1994 | Andersen et al. .............. 623/11 |
| 5,368,602 | 11/1994 | de la Torre ................. 606/151 |
| 5,433,996 | 7/1995 | Kranzler et al. .............. 623/11 |
| 5,462,781 | 10/1995 | Zukowski ..................... 623/11 |
| 5,468,242 | 11/1995 | Reisberg ..................... 606/151 |

OTHER PUBLICATIONS

D. F. Paling, F. T. I., Warp Knitting Technology, 1965, cover + pp. 107–143, Columbine Press.

*Primary Examiner*—James C. Cannon
*Attorney, Agent, or Firm*—Wolf, Greenfield & Sacks, P.C.

[57] ABSTRACT

A dual bar warp knit, hexagonal mesh fabric for use in hernia repair and to mend other muscle and tissue wall defects, produced according to a back bar pattern chain of 2/0 2/4 2/0 4/6 4/6 and a front bar pattern chain of 4/6 4/2 4/6 2/0 2/4 2/0.

11 Claims, 1 Drawing Sheet

.01"

# SURGICAL MESH FABRIC

FIELD OF INVENTION

The present invention relates to a surgical mesh fabric and, more particularly, to a surgical mesh fabric for use in laparoscopic procedures.

BACKGROUND OF THE INVENTION

Various prosthetic repair materials have been proposed to reinforce the abdominal wall and to close abdominal wall defects. Marlex mesh, a single bar warp knit, dual course Atlas polypropylene monofilament knit, is exemplary of an implant material that has been successfully used in hernia repair. Traditionally, prosthetic repair materials are placed in an open procedure where a two inch or longer incision is made through the abdominal wall, layers of healthy tissue are retracted to expose the void and then the rupture is filled or covered with the implantable fabric.

Recently, prosthetic surgical fabrics have been implanted laparoscopically which is a surgical procedure employing slender tubes (cannulas) that extend through narrow punctures in the abdominal wall. Because the abdominal cavity remains closed, the surgeon employs an illuminating optical instrument through one of the cannula to visualize the surgical site on a television monitor. Surgical instruments are manipulated by the surgeon through other cannula in the abdominal wall, as the location of the instruments are observed on the monitor, to place the prosthetic repair material over or in the defect.

A concern has been raised that light may reflect off of the fabric surface during laparoscopy, potentially impairing visualization of the prosthetic repair material and the underlying anatomy. Increasing the pore size of a mesh fabric may improve laparoscopic observability but also may diminish the physical properties that had suggested the implant for augmenting or repairing abdominal wall defects. Many large pore mesh fabrics are known, such as the various openworks described in Paling, Warp Knitting Technology (Columbine Press). Although a dual bar warp knit, hexagonal mesh is described by Paling in FIGS. 67f, 74 and 75 and at page 114, there is no indication or suggestion that such a fabric would be suitable as a prosthetic or that it would obviate the potential laparoscopic visualization concern.

Accordingly, there is a need for a mesh fabric suitable for hernia repair which combines the performance and physical characteristics of conventional prosthetic repair materials with good laparoscopic visibility.

SUMMARY OF THE INVENTION

The present invention is a dual bar warp knit, hexagonal mesh fabric that is particularly suitable for use in laparoscopic hernia repair, although it is contemplated for classical open procedures as well. The mesh fabric exhibits a favorable combination of physical and performance characteristics while still allowing the surgeon to see through the fabric during laparoscopy.

In one embodiment of the invention, the prosthetic repair material is formed of polypropylene monofilament threads that have been dual bar warp knitted into a large pore hexagonal mesh according to a back bar pattern chain of 2/0 2/4 2/0 4/6 4/2 4/6 and a front bar pattern chain of 4/6 4/2 4/6 2/0 2/4 2/0.

It is among the general objects of the invention to provide a prosthetic mesh which combines good physical and performance properties with acceptable laparoscopic visibility.

It is a further object of the invention to provide an implantable fabric for laparoscopically repairing a tissue or muscle wall defect such as an inguinal hernia.

Other objects and features of the present invention will become apparent from the following detailed description when taken in connection with the accompanying drawings. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which.

DESCRIPTION OF THE PREFERRED EMBODIMENT

The present invention is a surgical mesh fabric for reinforcing and closing soft tissue defects, and is particularly indicated for chest wall reconstruction and the repair of inguinal hernias. The mesh fabric is formed of a biologically compatible, flexible and strong implantable material. The dual bar (two partially threaded guide bars) warp knit, diamond fabric includes large openings between adjacent yarn columns, ensuring good visibility of the underlying anatomy when the fabric is used in laparoscopic procedures without sacrificing mechanical properties of the mesh. The porous character of the fabric allows tissue infiltration to incorporate the prosthetic. The dual bar construction provides a stable fabric which is resistant to unraveling or running. The knitted fabric is sufficiently strong to prevent pullout of anchoring sutures. The flexible fabric may be collapsed into a slender configuration, such as a roll, which can be supported in, and advanced through, a narrow laparoscopic cannula.

When knitted from polypropylene monofilament yarns, the porous prosthetic repair fabric allows a prompt fibroblastic response through the interstices of the mesh, forming a secure fibrous/prosthetic layer. The polypropylene monofilament fabric is inert in the presence of infection, non-wettable and has a low foreign body reaction.

Figure 1:
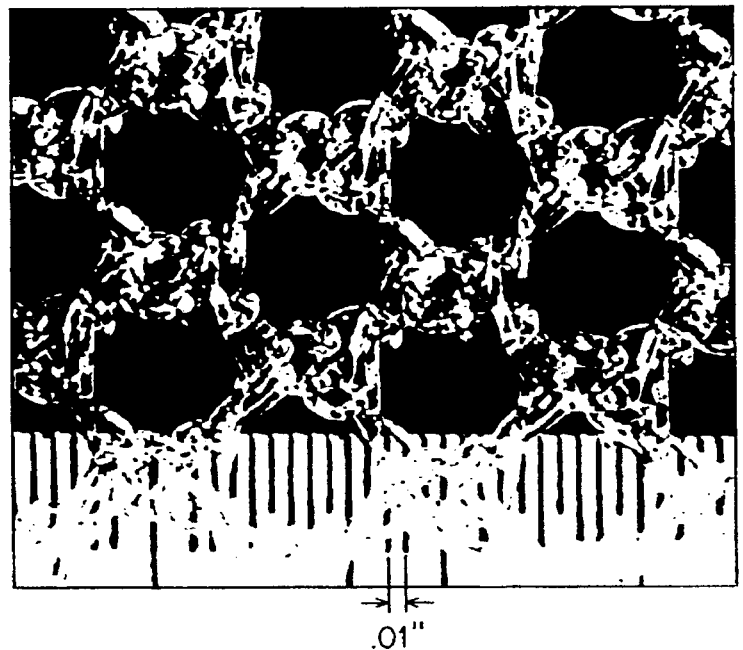
FIG. 1 is a photomicrograph (approximately 11× mag.) of a warp knit dual bar, hexagonal mesh fabric according to the present invention.
Figure 2:
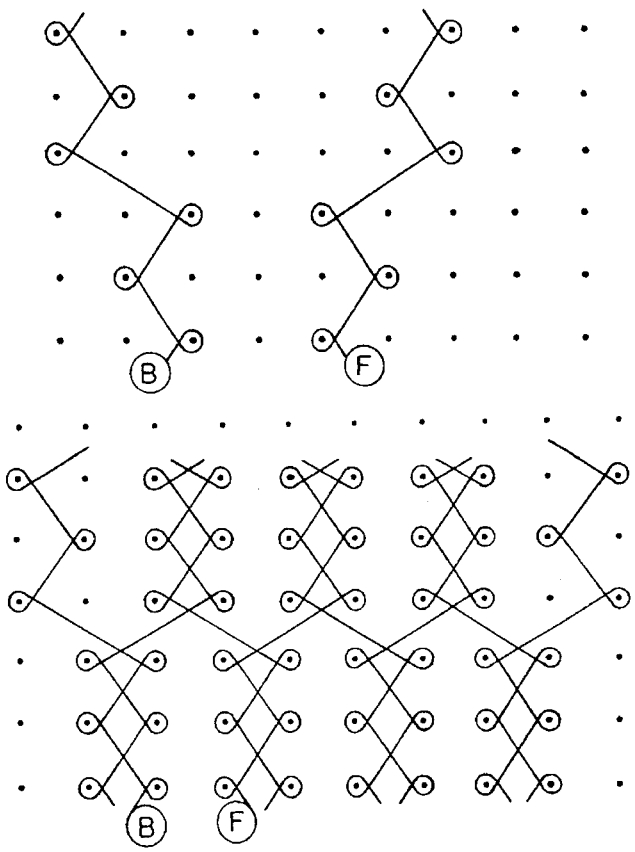
FIG. 2 is the chain lapping pattern for the mesh fabric shown in FIG. 1.

The fabric, illustrated in the lapping pattern and photomicrograph of FIGS. 1–2, is a two bar warp knit, hexagonal mesh produced by using two partially threaded guide bars to knit the same pattern over three needles in a six course repeat. The column portions are formed by two separate ends of yarn crossing each other on two needles with the crossover portion traversing across a third needle. If one end of yarn breaks, a back up yarn will secure the fabric from at least two yarns away to prevent unraveling of the mesh. A selvage edge may be formed using a double end of yarn and knitting over two empty needle spaces on each side of the band defining the band width. The tension on the yarns may be greater when knitting the selvage as compared to the body of the mesh to encourage the denser selvage to curl over itself in the direction of body of the mesh, forming a rigid edge member which can be grasped with laparoscopic tools during placement to help position the implant relative to the surgical site. Although a denser, knitted selvage is described, other arrangements of one or more edges of the fabric may be employed as would be apparent to one of skill in the art.

Following knitting, the fabric is washed with water and a cleaning agent, such as Triton X-100, to remove processing lubricant. The mesh is dried at low temperature. The fabric is heat set under tension, in a crochet hoop or tentering frame, to provide the desired pore configuration. Preferably, the pores have an elongated diamond to square shape, although other shapes including, without limitation, diamond, square, circular and near-circular, are contemplated so long as the porous fabric provides good visibility when used in laparoscopy while retaining the physical and performance properties necessary for an effective prosthetic repair of inguinal and chest wall defects.

Although the surgical mesh fabric preferably is knit from monofilament polypropylene, other monofilament and multifilament yarns that are biologically compatible may also be suitable as would be apparent to one of skill in the art. Fabric parameters, such as quality, stretch, and yarn size may vary depending upon the application. In a representative embodiment, the fabric is formed of 0.006 inch polypropylene monofilament yarn (160 denier) knitted on a 36 gauge machine, although other gauges are contemplated. The mesh sheets may be knitted in twelve inch widths, although other dimensions are contemplated. The surgeon may cut the mesh into smaller pieces or shapes, preferably with heated or ultrasonic instruments, to melt and seal the edges of the fabric.

EXAMPLES

The following examples are illustrative only and are not intended to limit the scope of the present invention.

Physical properties of a representative two bar warp knit, hexagonal mesh fabric were evaluated and compared to conventional mesh fabrics. The tested mesh fabric was formed in a Mayer RM6 knitter under the following parameters:

| # of ends in body | 210 |
|---|---|
| # of ends in selvage | 14 |
| runner length | 96" |
| quality | 16" |
| take-up B/A | 56/49 |
| pattern chain | 2/0 2/4 2/0 4/6 4/2 4/6 FB |
| | 4/6 4/2 4/6 2/0 2/4 2/0 BB |
| gauge | 36 |
| width | 12" |
| lubricant | mineral oil |

Physical and performance characteristics were tested including mesh thickness, pore size, mesh density, stiffness, tensile strength, suture pullout, burst strength and tear resistance. Testing methodology and results appear below.

Mesh Thickness: A 6"×6" sample of mesh was placed on a standard fabric thickness gauge with a 1.29 inch diameter pressure foot and 10 oz. weight. The thickness was measured by lowering the foot on the middle of the sample and reading the thickness from the dial gauge, one reading per sample, to the nearest 0.001 inch.

Pore Size: A sample of mesh was placed on an optical measurement device. The area of a shape that closely approximated the shape of a pore was calculated following acquisition of several reference points.

Mesh Density: The weight of a 5"×5" piece of mesh was determined to the nearest 0.1 gram. The mesh was then placed in a partially filled graduated cylinder of water. After removal of air bubbles, the volume of displaced water was recorded to the nearest 0.1 cc. Density was calculated as:

weight (grams)/volume water displaced (cc)–grams/cc

Minimum Suture Pullout (Suture Tear Resistance): A monofilament polypropylene suture (size 3.0 or larger) was placed 2 mm from the edge of the sample. The mesh was clamped in the lower jaw and the suture was attached to the upper jaw of an Instron Tensile Tester. The suture was then pulled out of the mesh at a rate of 5" per minute with an initial jaw separation of 2–2.5". The peak force required to pull out the suture was recorded. Each mesh was tested in two directions with the direction of lowest strength being reported here.

Burst Strength: A 6"×6" piece of mesh was clamped in the fixture of a standard Mullen Burst Tester. Hydraulic pressure was slowly increased causing a rubber diaphragm to inflate, contact the mesh, and burst the mesh. The peak pressure (psi) required to burst the mesh was recorded.

Minimum Tear Resistance: A 3.5" slit was cut parallel to the long dimension of a 3"×8" piece of mesh. The slit was cut at the middle of one 3" side extending 3.5" into the sample. One "leg" was placed in the lower jaw and one "leg" in the upper jaw of an Instron Tensile Tester. The sample was then pulled and a 3" tear completed. The peak force (lbs) required to tear the sample was recorded. Each mesh was tested in 4 different directions with the direction with lowest strength being reported here.

Minimum Tensile Strength: A 1"×6" sample of mesh was placed in the jaws of an Instron Tensile Tester with the long axis of the sample vertical. The sample was then pulled to break at a constant rate of traverse of 12 inches/minute with a jaw pressure of 60 psi and a gauge length of 2 inches. The force at break (lbs) was recorded. Each mesh was tested in both directions with the direction of lowest strength being reported here.

Stiffness: A 1"×6" sample of mesh was placed in the clamping fixture of a Tinius Olsen Stiffness Tester. Once the sample had been mounted and the instrument zeroed, a force was applied to the specimen with a metal rod causing the sample to bend. At 10 degree increments of angular deflection, the percent load scale reading was recorded minus the initial percent load scale reading. The load (lbs) at each deflection angle was calculated as follows:

| $P = L \times M/S$ where | P = Pounds Load (lbs) |
|---|---|
| | L = Load Scale reading (%) |
| | M = Bending Moment (in lbs) |
| | S = Bending Span (in) |

The pounds load at a 40° angle was chosen as the value for comparison since it is about mid-way in the range of angular deflection (0°–90°).

TABLE I

| TEST<br>n = 30 unless otherwise noted | VISILEX<br>Mean ± SD | MARLEX<br>Mean ± SD | PROLENE<br>Mean ± SD | MERSILENE<br>Mean ± SD |
|---|---|---|---|---|
| Thickness (inches) | 0.034 ± 0.001 | 0.027 ± 0.001 | 0.025 ± 0.001 | Not Tested |
| Average Large Pore Area (in²) | 0.0038 ± 0.0002 | 0.0008 ± 0.0001 | 0.0013 ± 0.0001 | Not Tested |
| Mesh Density (grams/cc) | 0.8 ± 0.04 | 0.93 ± 0.02 | 0.93 ± 0.02 | Not Tested |
| Stiffness at 400 Bend (lbs) | 0.018 ± 0.005<br>N = 29 | 0.013 ± 0.002<br>N = 6 | 0.036 ± 0.005 | Not Tested |
| Minimum Tensile Strength (lbs.) | 38.97 ± 2.45 | 32.85 ± 3.19 | 54.4 ± 6.58 | 15.64 ± 0.71 |
| Minimum Suture Tear Resistance (lbs) | 8.32 ± 1.32 | 5.25 ± 0.78 | 7.53 ± 3.42 | Not Tested |
| Burst Strength (psi) | 147 ± 6 | 162 ± 10 | 250 ± 9 | 77 ± 3 |
| Minimum Tear Resistance (lbs) | 11.64 ± 1.11 | 6.63 ± 2.38 | 5.42 ± 5.87 | Not Tested |

It should be understood that the foregoing description of the invention is intended merely to be illustrative thereof and that other equivalents, embodiments and modifications of the invention may apparent to those of skill in the art without departing from the scope or spirit thereof.

What is claimed is:

1. As a prosthetic for repairing living animal tissue, body wall or muscle defects, a biologically compatible, implantable dual bar warp knit, hexagonal mesh produced according to a back bar pattern chain of 2/0 2/4 2/0 4/6 4/2 4/6 and a front bar pattern chain of 4/6 4/2 4/6 2/0 2/4 2/0.

2. The implantable dual bar warp knit, hexagonal mesh recited in claim 1 formed of polypropylene monofilament yarns.

3. The implantable dual bar warp knit, hexagonal mesh recited in claim 1 including a body portion and a selvage that is more rigid than said body portion.

4. The implantable dual bar warp knit, hexagonal mesh recited in claim 1 wherein said more rigid selvage is curled.

5. The implantable dual bar warp knit, hexagonal mesh recited in claim 1 including elongated diamond to square pores.

6. The implantable dual bar warp knit, hexagonal mesh recited in claim 1 including circular pores.

7. The implantable dual bar warp knit, hexagonal mesh recited in claim 1 including near circular pores.

8. The implantable dual bar warp knit, hexagonal mesh recited in claim 1 including square pores.

9. The implantable dual bar warp knit, hexagonal mesh recited in claim 1 including diamond pores.

10. The implantable dual bar warp knit, hexagonal mesh recited in claim 1 including yarn columns formed by two separate ends of yarn that cross each other on two needles with the crossover portion traversing across a third needle, wherein in one end of yarn breaks a back up yarn will secure the fabric from at least two yarns way to prevent unraveling of the mesh.

11. The implantable dual bar warp knit, hexagonal mesh recited in claim 1 wherein said mesh is supported within a laparoscopic cannula.

* * * * *